United States Patent [19]

Devine et al.

[11] Patent Number: 5,720,438
[45] Date of Patent: Feb. 24, 1998

[54] MOBILE APPARATUS AND PROCESS FOR TREATING INFECTIOUS WASTE

[76] Inventors: Thomas J. Devine; Charlie Wolfgram, both of 11111 Katy Freeway, #600, Houston, Tex. 77079

[21] Appl. No.: 587,156

[22] Filed: Jan. 16, 1996

[51] Int. Cl.$^6$ .................................................. B02C 19/12
[52] U.S. Cl. ........................ 241/21; 241/29; 241/606; 422/27
[58] Field of Search .................... 422/27, 292; 241/606, 241/21, 29, 101.74, 101.741

[56] References Cited

U.S. PATENT DOCUMENTS

| | | |
|---|---|---|
| 3,547,577 | 12/1970 | Lovercheck . |
| 4,578,185 | 3/1986 | Wilson et al. . |
| 4,618,103 | 10/1986 | Wilson et al. . |
| 4,884,756 | 12/1989 | Pearson . |
| 5,054,696 | 10/1991 | Mennel et al. . |
| 5,077,007 | 12/1991 | Pearson . |
| 5,078,965 | 1/1992 | Pearson . |
| 5,116,574 | 5/1992 | Pearson . |
| 5,173,257 | 12/1992 | Pearson . |
| 5,346,142 | 9/1994 | Miller et al. .......................... 241/29 |
| 5,516,049 | 5/1996 | Zoncada . |
| 5,570,845 | 11/1996 | Lewis et al. . |

Primary Examiner—Mark Rosenbaum
Attorney, Agent, or Firm—Kenneth A. Roddy

[57] ABSTRACT

A mobile self-contained apparatus and process for grinding, grating, macerating, chemically disinfecting, and drying infectious waste material on-site. A trailer contains a hopper and a system of grinder/graters, enclosed conveyors, drying and filter apparatus, and sources of power, chemical disinfectant, and fresh water. Bagged infectious waste material in a cart is lifted and dumped into a hopper, fed to a first grinder/grater, ground and grated into particles, immersed in a sodium hypochlorite (hypochlorous acid) chemical disinfectant solution, and conveyed by an enclosed upwardly inclined screw conveyor to a second grinder/grater. The particles are sprayed one or more times with the disinfectant and thoroughly mixed together as they are conveyed in the inclined conveyor and are dumped from the inclined conveyor into the second grinder/grater operating at a higher speed than the first and further ground, grated, and macerated into smaller particles, and air dried to produce a dry confetti-like material which is unrecognizable as to the source. The confetti-like material is conveyed by an enclosed horizontal screw conveyor to an enclosed vertical screw conveyor where it is passed upwardly to an enclosed rotatable discharge screw conveyor which discharges the confetti-like material into a receptacle. The enclosed system operates under negative pressure produced by a suction fan which draws the air within the system through a hepa-filter to remove chemical fumes, airborne dust, odors and bacteria.

7 Claims, 4 Drawing Sheets

MOBILE APPARATUS AND PROCESS FOR TREATING INFECTIOUS WASTE

BACKGROUND OF THE INVENTION

1. Field of the Invention

This invention relates generally to waste material treatment apparatus and methods, and apparatus, and more particularly to a self contained mobile apparatus and improved process for grinding, grating, macerating, chemically disinfecting, and drying medical waste materials on-site at health care related facilities.

2. Brief Description of the Prior Art

The following terms, as used herein, are recognized in government regulations, and in the trade, as distinguishing one type of medical waste treatment process from another.

"STERILIZATION" is a process which destroys all microbial life including large numbers of bacterial endospores. "DISINFECTION" is a somewhat less lethal process than sterilization which destroys or inactivates viruses, fungi, and bacteria (but not necessarily their endospores) on inanimate surfaces. "CHEMICAL DISINFECTION" is the use of a chemical agent to reduce significantly the numbers of active microorganisms (but not necessarily their endospores) from the surfaces of inanimate objects. "INCINERATION" is the process of burning waste in an incinerator. "AUTOCLAVING" is the process wherein waste material is sterilized with steam in an enclosed compartment. "UNRECOGNIZABLE" means that the original appearance of the waste item has been altered such that neither the waste nor its source can be identified. "GRINDING" is the physical process which pulverizes materials, thereby rendering them as unrecognizable, and for sharps, reduces the potential for the material to cause injuries such as puncture wounds. "SHREDDING" is the physical process which cuts, slices, or tears materials into small pieces. "CHLORINE DISINFECTION/MACERATION" is the process of shredding waste in the presence of a chlorine solution under negative pressure.

The description of infectious medical waste and the approved methods of handling this waste varies from state to state. Generally, infectious medical waste, or "red bag" waste is defined as including body fluids, microbiological waste, pathological waste, sharps, and animal waste. The term "red bag" is the red bag that hospitals are required by government regulations to use for containing infectious medical waste to clearly identify the contents. Red bag waste does not include radioactive materials, large quantities of chemicals, or large metal objects.

A "$\log_{10}$ reduction" is a mathematically defined unit used in reference to level or degree of microbial inactivation. A 4 $\log_{10}$ reduction represents a 99.99% reduction in the numbers of active microorganisms, while a 6 $\log_{10}$ reduction represents a 99.9999% reduction in the numbers of active microorganisms. A process to meet the criteria set out in regulatory guidelines for "on-site" processing of infectious medical waste requires that it be disinfected to guarantee a 4 $\log_{10}$ reduction or 99.99%, and must yield a product residue which is unrecognizable as to the source.

It is important to point out the basic microbiology and chemistry as it relates to "sterilization" and "disinfection". As discussed above, "sterilization" destroys all microbial life including large numbers of bacterial endospores. On the other hand, "disinfectants", if properly used, will eliminate all pathogenic vegetative organisms but not all endospores. Since most endospore formers are non-pathogenic, an effective disinfectant will kill the broad range of potential pathogens. Hypochlorites (calcium and sodium) are relatively inexpensive, fast acting, and have a broad spectrum of anti-microbial activity. Their use as disinfectants is limited by their corrosiveness, inactivation by organic matter, and relative instability. The microbiocidal activity of chlorine is largely attributed to hypochlorous acid (HOCl). Hypochlorite ion (OCl) posses about 1/80th the germicidal capacity of hypochlorous acid (HOCl). The chemical reaction which causes disassociation of hypochlorous acid (HOCl) to the less microbiocidal form hypochlorite ion (OCl), Cl2, and various sodium salts is dependent on pH. As the pH increases, more hypochlorite ion (OCl) is formed and the microbiocidal activity decreases. As the pH decreases, the concentration of hypochlorous acid (HOCl) increases and the microbiocidal activity increases. Hypochlorous acid (HOCl) is the "microbiocidal" component of the disassociated end products of sodium hypochlorite (NaOCl). The production of hypochlorous acid (HOCl) and resultant microbiocidal activity is at its greatest when the pH is in the range of from 4 to 6.

At a pH of 1.0 to 4.5, the reaction is driven to 90% to 95% Cl2. At a pH range of 4.5 to 6.0, the reaction is driven to 90% to 95% hypochlorous acid (HOCl). At a pH range greater than 6.0, the reaction is driven to 80% to 95% hypochlorite ion (OCl) and is less microbiocidal. If a sodium hypochlorite (NaOCl) disinfectant is adjusted to a pH of 4.0 to 6.0, the microbiocidal properties are enhanced to a factor of more than 100×.

The present invention utilizes a sodium hypochlorite (NaOCl) solution adjusted to a pH of from about 4.0 to 6.0 to increase the hypochlorous acid (HOCl) component and significantly increase the microbiocidal activity of the disinfectant.

Traditionally, the majority of infectious medical waste has either been "incinerated" or "autoclaved" to render the end product non-infectious and unrecognizable. The residue of incineration has been deposited in landfills as fly ash or bottom ash. Incineration has become an unacceptable method due to recent air quality standards and problem areas concerning air emissions during incineration such as carcinogenic organic, dioxins, and furans, as well as acid gases. The controversy over incineration has resulted in substantial public opposition to the construction of new incinerators and frequent demonstrations demanding closure of existing incinerators.

"Autoclaving", wherein the bulk waste material is sterilized with steam in an enclosed compartment, also has many objectionable characteristics. Autoclaving alone does not change the physical appearance of the waste, resulting in uncertainty and fear among subsequent handlers. In many cases, autoclaved materials have been rejected at landfills. The cost of construction and operation precludes autoclaving as an acceptable alternative for treating large volumes of infectious medical waste. Other methods such as chemical disinfection, microwaving, thermal or dry heat inactivation, chlorine disinfection/maceration, and moist heat disinfection have been proposed. Most of these other methods either cannot meet the total volume requirements and/or do not significantly reduce the microbial colony count to acceptable levels.

Another major problem with prior art treatment methods is that the process is usually carried in large treatment plants which are built or fixed at a location remote from the waste generating facility, because of their requirements for large amounts of power, fluids, heat, and potential of fluid residue hazards.

Thus, another important objection to incineration, autoclaving, and other traditional methods of infectious waste treatment and disposal is the logistics of transporting the infectious medical waste material from the waste generating facility to the incinerator, autoclaving facility, microwaving facility, or chemical treatment plant over public thoroughfares and highways.

Federal regulations are very strict if infectious medical waste is taken away from the premises of the hospital or health care facility ("off-site") for incineration or other methods of disposal. The U.S. Department of Transportation has an entire set of regulations including special handling, recording, packaging, and storage, which must be followed by the health care facility, the hauler, and the receiver of the infectious waste. The health care facility must also have liability insurance, in the event of an accident before the waste materials are destroyed. However, if the waste materials are processed on the health care facility premises ("on-site"), there are substantially fewer requirements on the health care facility. Thus, the health care facility is faced with either transporting the infectious waste to a remote treatment plant or with a massive capital expenditure to build an on-site waste treatment system.

There are several patents which disclose various waste treatment apparatus and sterilization and disinfection processes, most of which require a large system of apparatus fixed-in-place on-site (not mobile) and require placement in close vicinity to sources of supply of power, fluids, and heat, or placement at a remote site which requires providing these sources of supply at the remote location. Thus, most of these systems require the health care facility to install the system on-site or to transport the waste to a remote location.

Miller et al, U.S. Pat. No. 5,346,142 discloses a fixed-in-place apparatus and method for shredding and sterilizing medical waste material wherein the waste material is initially shredded by a primary shredder, sprayed with a sterilant and mixed in a screw conveyor, fed into a second higher speed shredder for further shredding, fed into a second screw conveyor for further mixing, fed into a turbo blender which further mixes and shatters any substantially sized particles remaining after shredding and moves it into a conveyor, and it is finally discharged as unrecognizable waste material. The disclosure is silent as to the type of sterilant used.

Pearson, U.S. Pat. Nos. 5,173,257 and 5,116,574 disclose a fixed-in-place chemical disinfection process and apparatus for the treatment of infectious medical waste utilizing ozone wherein the medical waste is subjected to an ozone liquid or gas disinfectant, shredded, fed to a separation tank, fed to from 1 to 6 reactor vessels where ozone gas bubbles pass through the infectious waste material. The ozone disinfection process requires contacting times of from about 5 to about 45 minutes to effectively disinfect the waste.

Pearson, U.S. Pat. Nos. 5,077,007 and 5,078,965 disclose a fixed-in-place chemical disinfection process and apparatus for the treatment of infectious medical waste utilizing ozone wherein the medical waste is subjected to an ozone liquid or gas disinfectant, shredded, fed to a separation tank, fed to a fluidized bed reactor vessel where ozone gas bubbles pass through the infectious waste material. The ozone disinfection process requires contacting times of from about 5 to about 45 minutes to effectively disinfect the waste.

Mennel et al, U.S. Pat. No. 5,054,696 discloses a fixed-in-place medical waste disposal system for disposing of biologically contaminated waste situated inside a rigid, form-stable container which includes a screw auger which shreds the material and may mix the shredded mass with a liquid disinfectant solution. The auger transports the mass to a hammermill which disintegrates the shredded mass into an unrecognizable particulate. The disclosure is silent as to the type of disinfectant fluid used.

Pearson, U.S. Pat. No. 4,884,756 discloses a fixed-in-place infectious waste treatment system wherein the waste is placed into a feeding channel and moved by a ram into a series of shredders and is then gravity fed into a disinfecting fluid contained within an enclosed decontamination and separation device. The disclosure is silent as to the type of disinfectant fluid used or whether the material is discharged in a soaked condition.

Wilson et al, U.S. Pat. No. 4,618,103 discloses a relatively small hospital waste disposal system wherein a hammermill, a disinfectant solution, and separator tank divided into collecting pools which are adapted for connection to a sewer for disposing of the disinfectant are contained in a sealed cabinet which is placed in patient wards of a hospital. The disclosure is silent as to the type of disinfectant solution used.

Wilson et al, U.S. Pat. No. 4,578,185 discloses a fixed-in-place hospital waste disposal system wherein an inclined belt conveyor transfers waste materials through slitted curtains and drops it into a shredder while it is sprayed with a sodium hypochlorite solution having a pH of 8.5 and then enters a hammermill. The particles are then fed through a particle separator where solid particles are separated from the liquid disinfectant for independent evacuation. The liquids are evacuated to the sewer system and the solids are deposited in a cart. The system also includes vacuum ventilation elements to maintain any released bacteria or particles in the system until completely processed. As pointed out above, when the pH range of sodium hypochlorite is greater than 6.0, the reaction is driven to 80% to 95% hypochlorite ion (OCl) and is less microbiocidal than a solution with a pH of 6.0 or less.

Lovercheck, U.S. Pat. No. 3,547,577 discloses a wheeled vehicle for processing and sterilizing refuse such as trash and domestic garbage which carries a shredding machine that shreds the garbage which is then heated by a heater, a compactor which compresses the shredded material into briquettes, and a tank wherein the briquettes are contacted with a microbiocidal gas such as ethyelene oxide, propylene oxide, methyl bromide, or betapropiolactone.

The present invention overcomes the problems discussed above and provides a very cost effective alternative to transporting infectious waste and building new on-site waste treatment systems for each health care facility.

The present invention is distinguished over the prior art in general, and these patents in particular by a mobile self-contained apparatus and process for grinding, grating, macerating, chemically disinfecting, and drying infectious waste material on-site. A trailer contains a hopper and a system of grinder/graters, enclosed conveyors, drying and filter apparatus, and sources of power, chemical disinfectant, and fresh water. Bagged infectious waste material in a cart is lifted and dumped into a hopper, fed to a first grinder/grater, ground and grated into particles, immersed in a sodium hypochlorite (hypochlorous acid) chemical disinfectant solution, and conveyed by an enclosed upwardly inclined screw conveyor to a second grinder/grater. The particles are sprayed one or more times with the disinfectant and thoroughly mixed together as they are conveyed in the inclined conveyor and are dumped from the inclined conveyor into the second grinder/grater operating at a higher speed than the first and further ground, grated, and macerated into smaller particles, and air dried to produce a dry confetti-like material which is unrecognizable as to the source. The confetti-like material is conveyed by an enclosed horizontal screw conveyor to an enclosed vertical screw conveyor where it is passed upwardly to an enclosed rotatable discharge screw conveyor which discharges the confetti-like material into a receptacle. The enclosed system operates under negative pressure produced by a suction fan which draws the air within the system through a hepa-filter to remove chemical fumes, airborne dust, odors and bacteria.

SUMMARY OF THE INVENTION

It is therefore an object of the present invention to provide a mobile self-contained apparatus and process for grinding, grating, macerating, chemically disinfecting, and drying infectious waste material.

It is another object of this invention to provide a mobile self-contained apparatus and process for grinding, grating, macerating, chemically disinfecting, and drying infectious waste material which is a very cost effective alternative to transporting infectious waste and building new on-site waste treatment systems for individual health care facilities.

Another object of this invention is to provide a mobile self-contained apparatus and process for on-site grinding, grating, macerating, chemically disinfecting, and drying infectious waste material which eliminates the potential hazards of transporting untreated infectious waste material from the waste generating facility to a remote treatment plant over public thoroughfares and highways.

Another object of this invention is to provide a mobile self-contained apparatus and process for grinding, grating, macerating, chemically disinfecting, and drying infectious waste material which renders it into a substantially dry confetti-like material unrecognizable as to its source which can then be safely transported to a landfill along with general waste from the health care facility.

Another object of this invention is to provide a mobile self-contained apparatus and process for grinding, grating, macerating, chemically disinfecting, and drying infectious waste material which utilizes a sodium hypochlorite (NaOCl) disinfectant solution adjusted to a pH of about 4.0 to about 6.0 and final concentration of 2,500 ppm hypochlorous acid and will consistantly produce at least a 4 $Log_{10}$ reduction or 99.99%, and in most cases, a 6 $Log_{10}$ reduction or 99.9999% reduction in the numbers of active microorganisms.

Another object of this invention is to provide a mobile self-contained apparatus and process for grinding, grating, macerating, chemically disinfecting, and drying infectious waste material which can process from 1,500 to 3,000 pounds of waste per hour.

A further object of this invention is to provide a mobile self-contained apparatus and process for grinding, grating, macerating, chemically disinfecting, and drying infectious waste material which is economical to manufacture and operate and does not require outside sources of power, fluids, or heat.

A still further object of this invention is to provide a mobile self-contained apparatus and process for grinding, grating, macerating, chemically disinfecting, and drying infectious waste material which is quiet in operation, non-polluting, and does not require the assistance of any medical personnel.

Other objects of the invention will become apparent from time to time throughout the specification and claims as hereinafter related.

The above noted objects and other objects of the invention are accomplished by a mobile self-contained apparatus and process for grinding, grating, macerating, chemically disinfecting, and drying infectious waste material on-site. A trailer contains a hopper and a system of grinder/graters, enclosed conveyors, drying and filter apparatus, and sources of power, chemical disinfectant, and fresh water. Bagged infectious waste material in a cart is lifted and dumped into a hopper, fed to a first grinder/grater, ground and grated into particles, immersed in a sodium hypochlorite (hypochlorous acid) chemical disinfectant solution, and conveyed by an enclosed upwardly inclined screw conveyor to a second grinder/grater. The particles are sprayed one or more times with the disinfectant and thoroughly mixed together as they are conveyed in the inclined conveyor and are dumped from the inclined conveyor into the second grinder/grater operating at a higher speed than the first and further ground, grated, and macerated into smaller particles, and air dried to produce a dry confetti-like material which is unrecognizable as to the source. The confetti-like material is conveyed by an enclosed horizontal screw conveyor to an enclosed vertical screw conveyor where it is passed upwardly to an enclosed rotatable discharge screw conveyor which discharges the confetti-like material into a receptacle. The enclosed system operates under negative pressure produced by a suction fan which draws the air within the system through a hepa-filter to remove chemical fumes, airborne dust, odors and bacteria.

DESCRIPTION OF THE PREFERRED EMBODIMENT

Figure 1:
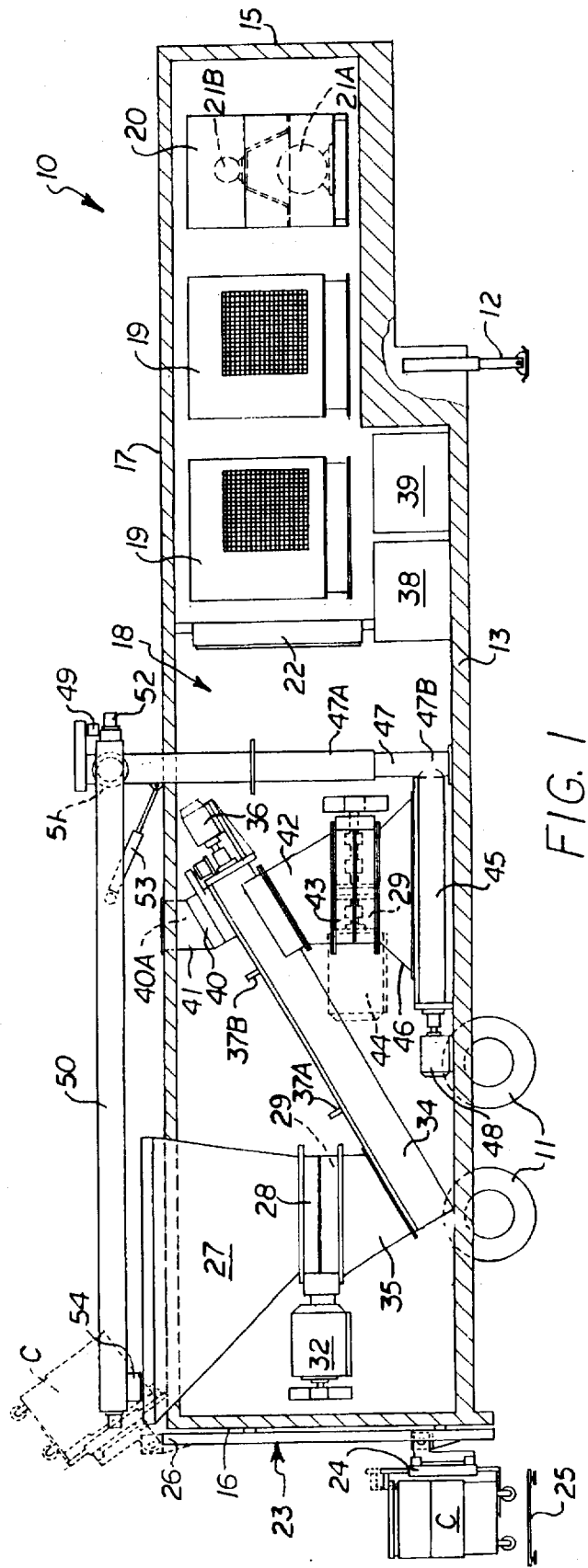
FIG. 1 is a side elevation of the mobile waste processing trailer which contains apparatus for processing waste materials in accordance with the present invention, the trailer being shown in cross section.
Figure 2:
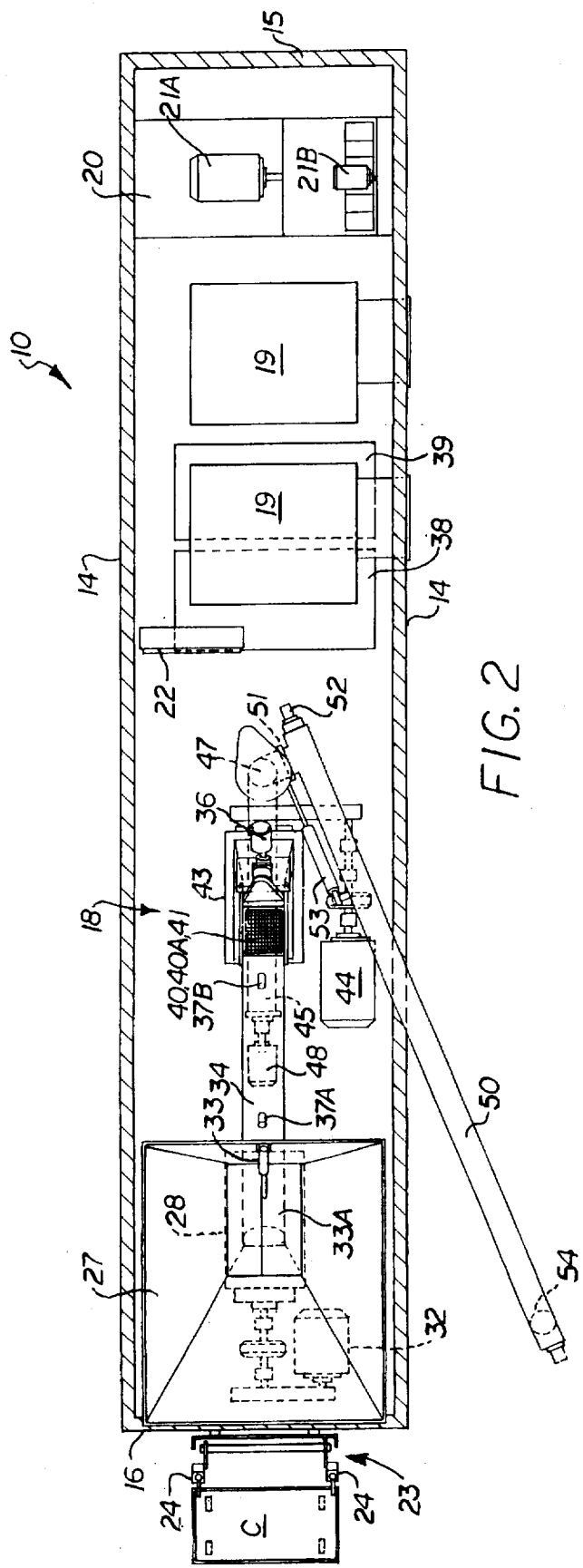
FIG. 2 is a top plan view showing the waste processing apparatus contained in the mobile waste processing trailer with the trailer shown in cross section.

Referring to the drawings by numerals of reference, there is shown in FIGS. 1 and 2, a mobile waste processing trailer 10 which contains a system of apparatus 18 for processing waste materials. The waste processing apparatus 18 is contained substantially within the enclosed wheeled trailer 10 which may be coupled to a truck tractor and transported to various job sites and health care related facilities such as hospitals, clinics, doctor's offices, etc., for processing waste materials, such as infectious medical waste material on-site. The trailer 10 has an elongated frame supported at the rear end by rear wheels 11 and at a forward end by extensible legs or jacks 12.

The trailer 10 has a floor or bottom wall 13, opposed side walls 14, front and rear walls 15 and 16, respectively, and a top wall 17 which surround and enclosure the waste processing apparatus 18 mounted inside with the exception of a discharge screw conveyor 50 which is disposed exterior of the trailer enclosure. The walls of the trailer 10 are formed of a suitable material and may be provided with suitable seals to form a secondary enclosure for containing spills and gases in the event of accidental leakage from the components inside. The walls of the trailer may also be insulated to control temperature and noise. As explained hereinafter, the discharge screw conveyor 50 can rotate 360° about a vertical axis and relative to the trailer to facilitate discharging the processed waste material into a convenient receptacle, such as a dumpster, compactor, or dump truck.

Referring still to FIGS. 1 and 2, the system of apparatus 18 mounted inside the trailer will be described. A pair of diesel driven generators 19 are mounted in the trailer to provide electrical power. A hydraulic supply system 20 is mounted in the trailer 10 and driven by motors 21A and 21B to provide hydraulic fluid under pressure for operating the hydraulically powered components described below. The particular drive motors and connecting drive mechanisms are conventional in the art, and therefore are not shown or described in detail. A control panel 22 inside the trailer 10 allows the operator to start and control the operation of the various components in the processing system.

A hydraulic lift mechanism 23 mounted on the rear end of the trailer 10 has a pair of hydraulic cylinders 24 that receive and grip a cart C which contains one or more bags of waste material to be processed. A load sensing scale 25 weighs the loaded cart C. The poundage of the waste material to be processed is determined after subtracting the weight of the cart. This data is fed into a computer database (not shown) and is used to calculate the proper amount of disinfectant to be used in the process. The hydraulic lift mechanism 23 raises and lowers cart C supported by the hydraulic cylinders 24. A dumping mechanism 26 at the top end of the hydraulic lift mechanism engages the cart and tips it over as the lift mechanism reaches it's uppermost extended position to dump out the bags of waste material contained in the cart C.

The top end of a hopper 27 extends through an opening in the top wall 17 of the trailer at the rear end of the trailer 10 adjacent to the upper end of the hydraulic lift mechanism 23 to receive the bags of waste material as they are dumped out of the cart C. A first modified grinding/grating machine 28 is connected to the bottom end of the hopper 27. The modified grinding/grating machine 28 has a conventional pair of rotating shafts with blades or blade knives along the length of the shafts, and is provided with a special grating plate 29 beneath the blade knives.

Figure 3:
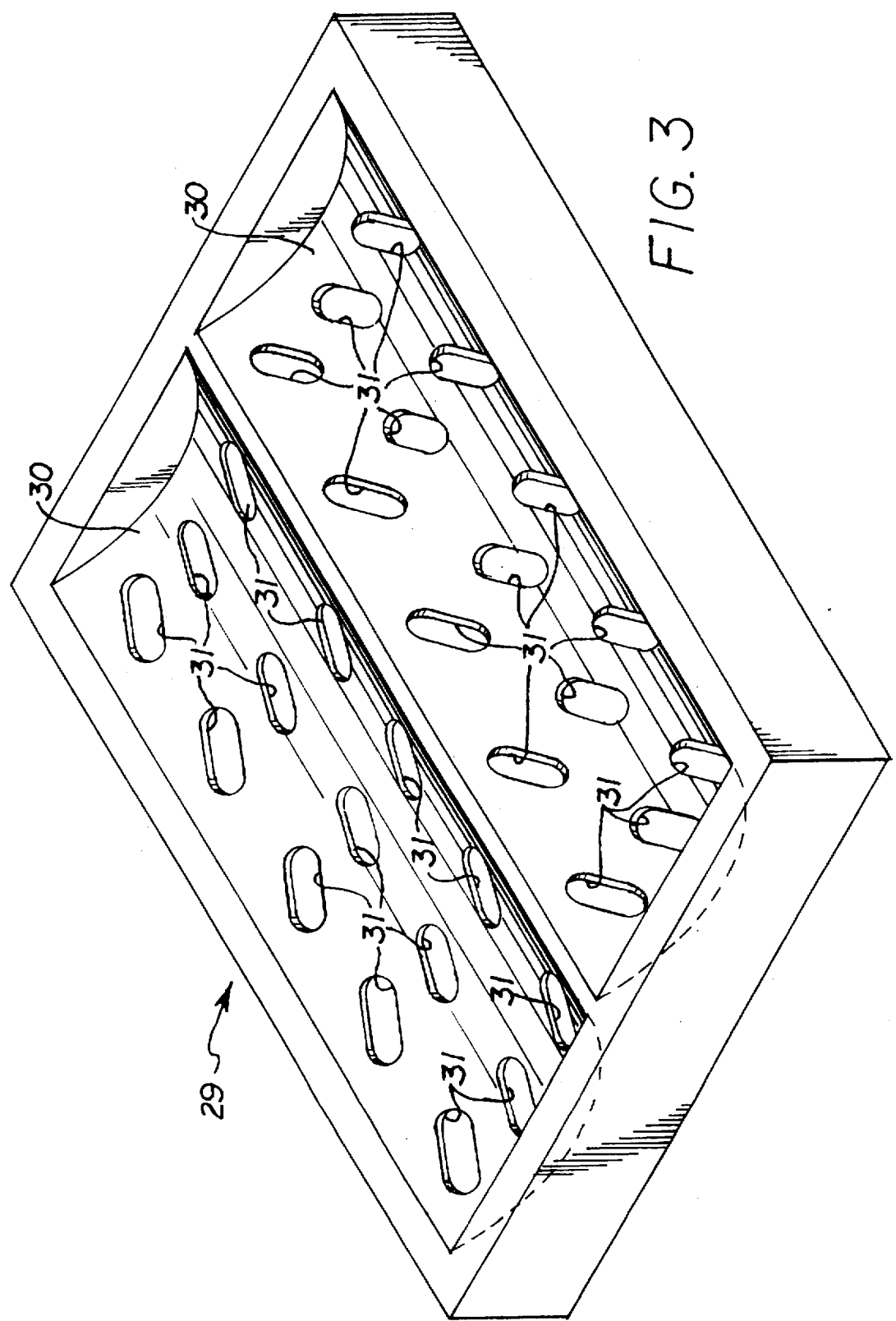
FIG. 3 is an isometric view of a grating plate which is used in the modified grinding/grating machinery of the apparatus.

As shown in FIG. 3, the grating plate 29 has a pair of concave surfaces 30 each having a plurality of apertures 31. In the modified grinding/grating machine 28, the blade knives not only cut and grind the bags of waste material, but also rotate against the apertured concave surfaces 30 of the grating plate 29 to grate the materials into particles of from ½" to 2" in size. The first modified grinding/grating machine 28 is preferably powered by a hydraulic motor 32 and connected to rotate the blade knives at about 46 rpm.

Referring again to FIGS. 1 and 2, a hydraulic ram 33 mounted at the top end of the hopper 27 is activated to move or pivot a pair of plates 33A downwardly into the hopper periodically, for example every 10 seconds, to press the materials down and facilitate engagement of the waste material with the rotating blade knives and grating plate of the modified grinding/grating machine 28.

An upwardly inclined screw conveyor 34 has a lower end disposed beneath the outlet of the modified grinding/grating machine 28 and is joined thereto by a shroud 35 to receive the ½" to 2" size particles of waste material. The screw conveyor 34 extends upwardly from the grinding/grating machine 28 at an angle and is completely enclosed. The lower end of the enclosed screw conveyor 34 serves as a vat for holding a quantity of chemical disinfectant in which the particles are immersed as they enter the conveyor, as explained hereinafter. In a preferred embodiment, the interior and exterior of the inclined screw conveyor 34 provided with an epoxy coating. The inclined screw conveyor 34 is preferably powered by hydraulic motor 36 connected to rotate the screw at about 85 rpm and continuously transport the particles away from the grinding/grating machine 28.

A first spray nozzle 37A is mounted near the lower end of the conveyor 34, and a second spray nozzle 37B is mounted near the discharge end of the conveyor. The nozzles 37A and 37B are connected through a calibrated mixing and pump system (not shown) to a fresh water tank 38 and a disinfectant tank 39 mounted inside the trailer. The tanks 38 and 39 are preferably formed of fiberglass. The disinfectant tank 39 is filled with a sodium hypochlorite (NaOCl) disinfectant solution adjusted to a pH of about 4.0 to about 6.0 to increase the hypochlorous acid (HOCl) component and significantly increase the microbiocidal activity of the disinfectant. The disinfectant inside the tank 39 may be continuously circulated by a pump (not shown) to insure a homogeneous mixture.

A three-stage hepa-filter 40 is connected to the upper end of the inclined screw conveyor 34 and a duct 41 connected with the hepa-filter extends through the top wall 17 of the trailer 10. A high-speed blower or suction fan 40A produces a vacuum or negative pressure in the enclosed system of preferably about 15 psi and draws the air in the enclosed system through the hepa-filter 40 and vents it to the atmosphere through the duct 41. The hepa-filter 40 contains a series of filter media which effectively captures and destroys chemical fumes, airborne dust particles, odors, and bacteria and the air discharged from the hepa-filter is safe to the environment and to humans.

As the ½" to 2" size particles of waste material leave the grinding/grating machine 28, they drop into the lower end of the inclined screw conveyor 34 and become immersed in the disinfectant solution contained in the lower end of the conveyor. As the previously immersed particles travel upward in the conveyor 34, they are sprayed with the disinfectant solution by the first nozzle 37A and become thoroughly mixed and saturated with the disinfectant solution, and after traveling a predetermined distance in the conveyor, the particles are once again sprayed with another application of the disinfectant solution by the second nozzle 37B disposed near the discharge end of the screw conveyor. The excess disinfectant drains down the inclined conveyor and is contained in its lower end which serves as the vat.

As the wet particles near the discharge end, the suction fan 40A and hepa-filter 40 removes and destroys any chemical fumes, airborne dust particles, odors, and bacteria.

The discharge end of the inclined conveyor 34 is connected by a shroud 42 to the top end of a second modified grinding/grating machine 43 which receives the particles as they drop from the discharge end of the conveyor 34. The second modified grinding/grating machine 43 has at least one conventional rotating shaft with blades or blade knives along the length of the shaft, and is provided with a special grating plate 29 beneath the blade knives. The second modified grinding/grating machine 43 operates at a substantially higher speed than the first machine 28 and, in a preferred embodiment has only have a single shaft, in which case, the grating plate 29 would only have one apertured concave surface. The grating plate 29 of the second grinding/grating machine is substantially similar to that previously described with reference to FIG. 3, except it has a single concave surface 30 with a plurality of apertures 31. The apertures 31 in the grating plate 29 used in the second grinding/grating machine 43 are sized to further grate particles to reduce them into particles of from ⅛" to ½" in size.

The second modified grinding/grating machine 43 is preferably powered by a 100 hp motor 44 connected to rotate the blade knives at about 1700–1900 rpm. The grating plate 29 is heated by the friction of the blade knives rotating at high rpm against the apertured concave surface 30 of the grating plate. Thus, in the second modified grinding/grating machine 43, the blade knives not only further reduce the size of the particles of waste material, but also act as fan blades to force the hot air generated by the heated grating plate 29 through the particles to dry the particles. Drying is further facilitated by the vacuum or negative pressure in the grinding/grating machine 43 produced by the fan 40A of the hepa-filter 40, since the machine 43 is part of the enclosed system. The hepa-filter 40 also effectively captures and destroys chemical fumes, airborne dust particles, odors, and bacteria which may be present during and after the second grinding and grating operation. The resulting product is a dry fluffy confetti-like material and is unrecognizable as to the source.

The inlet end of a horizontal screw conveyor 45 is disposed beneath the outlet of the second grinding/grating machine 43 and connected thereto by a shroud 46 to receive the dry confetti-like material and its discharge end is connected to the lower end of a tubular high-speed vertical conveyor 47. The horizontal screw conveyor 45 is preferably powered by a hydraulic motor 48 connected to rotate the screw at about 60 rpm and transport the confetti-like material to the vertical conveyor 47. The preferred tubular vertical conveyor 47 is powered by a hydraulic motor 49 connected to rotate the screw at about 120 rpm and swirl the dried confetti-like material in a spiral as it is transported vertically upward.

The vertical conveyor 47 is made in two tubular sections. The tubular upper section 47A of the vertical conveyor 47 extends through the top wall 17 of the trailer 10 and is rotatably connected to the tubular lower section 47B to rotate about the common vertical axis. A rotary seal (not shown) may be provided in the top wall 17 of the trailer 10 through which the upper section 47A of the vertical conveyor passes.

The inlet end of an elongate tubular discharge screw conveyor 50 is connected by a rotatable connection 51 to the upper end of the vertical conveyor 47. The preferred tubular discharge conveyor 50 is powered by a hydraulic motor 52 connected to rotate the screw at about 120 rpm. A hydraulic cylinder 53 is connected between the upper end of the vertical conveyor 47 and the tubular discharge conveyor 50 to pivot the discharge conveyor in a horizontal and vertical plane.

After reaching the upper end of the vertical conveyor 47, the dried confetti-like material enters the discharge conveyor 50 and is discharged through the outlet 54 at the outer end of the discharge conveyor. In a preferred embodiment, the height of the discharge conveyor 50 in a horizontal position is approximately 13 feet above the ground. The discharge conveyor 50 can rotate 360° about a vertical axis relative to the trailer and pivot upwardly or downwardly to facilitate discharging the confetti-like material into a convenient receptacle, such as a dumpster, compactor, or dump truck.

Figure 4:
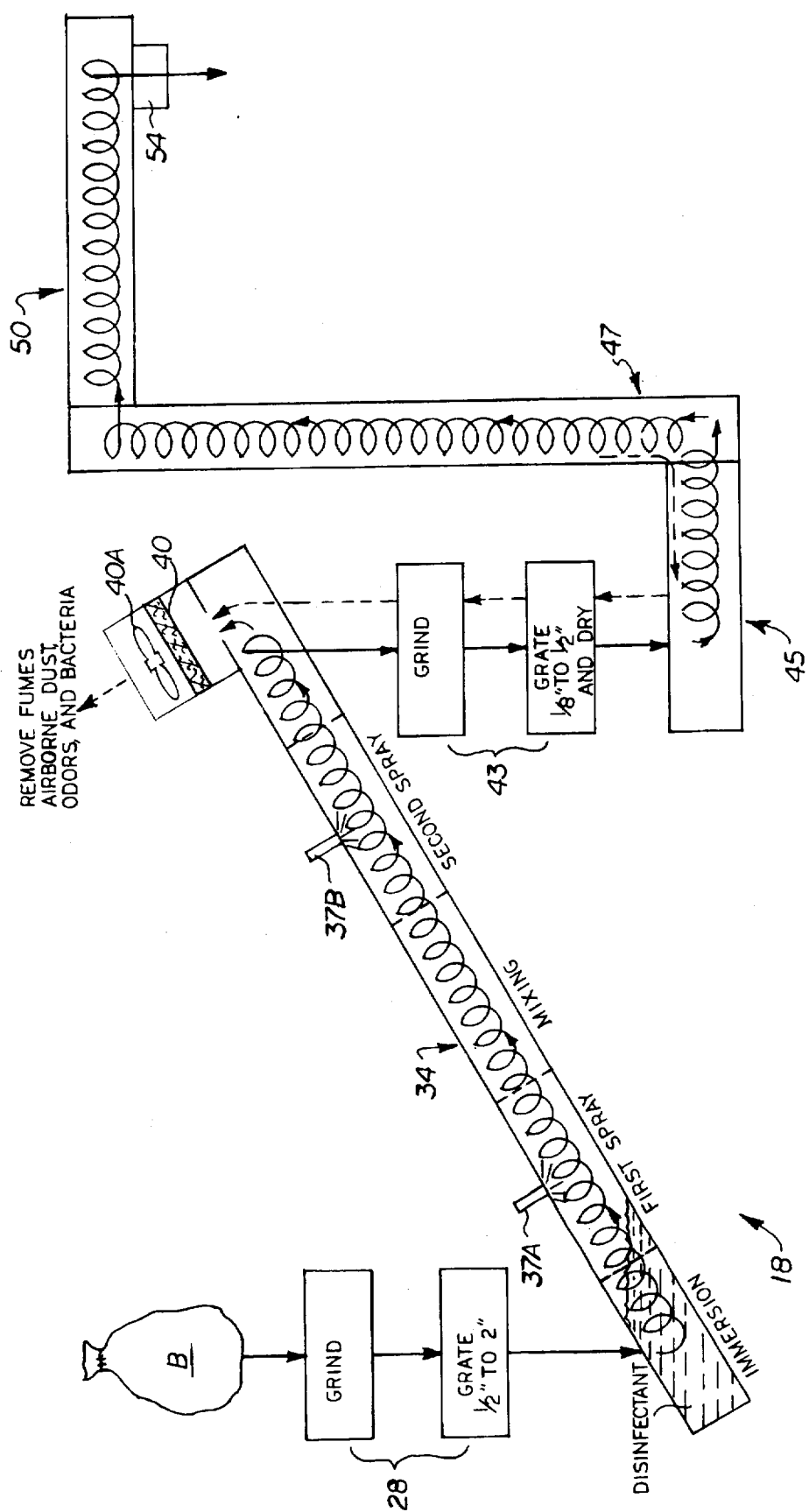
FIG. 4 is a flow diagram illustrating the steps in the process for grinding, grating, macerating and chemically disinfecting waste materials in accordance with the present invention.

Referring now additionally to FIG. 4, the major steps in the waste treatment process will be described. The mobile trailer apparatus is transported to a health care facility. The outlet end of the discharge chute 50 is positioned over a suitable receptacle, such as a dumpster, compactor, or dump truck. The bags B of infectious medical waste are loaded into carts C and the carts are weighed on the scale 25 (FIG. 1). After the weight of the bags of waste material has been determined and recorded, the amount and pH level of the sodium hypochlorite (NaOCl) disinfectant solution is adjusted to a pH of about 4.0 to about 6.0 to produce a final concentration of 2,500 ppm hypochlorous acid (HOCl). The hypochlorous acid serves as the microbiocidal component of the disinfectant solution. At this pH range, the hypochlorite ion (OCl) decreases and concentration of hypochlorous acid (HOCl) increases and thus, the microbiocidal activity of the sodium hypochlorite (NaOCl) solution increases. The speed of the conveyors is adjusted to provide a mixing time corresponding to the type and volume of material to be processed.

The bags B of infectious medical waste material are dumped into the hopper 27 and fed into the first modified grinding/grating machine 28. The modified grinding/grating machine 28 of the present invention is distinguished over conventional shredders used in other systems in that shredders cut, slice, or tear the materials into small pieces, whereas the modified grinding/grating machine not only cuts and grinds the bags of waste material, but also grates the materials against an apertured grating plate to grate the materials into particles of from ½" to 2" in size.

The grated particles of waste material drop into the lower end of the inclined screw conveyor 34 and become immersed in the disinfectant solution contained in the lower end of the conveyor. As the previously immersed particles are rotated and travel upward in the conveyor, they are sprayed with the disinfectant solution by the first nozzle 37A and become thoroughly mixed and saturated with the disinfectant solution, and after traveling a predetermined distance in the conveyor, the particles are once again sprayed with another application of the disinfectant solution by the second nozzle 37B disposed near the discharge end of the screw conveyor. Excess disinfectant drains down the inclined conveyor and is contained in its lower end which serves as the vat. In the present system, there is no drain which allows the chemical to escape onto the ground. The chemical volume is controlled by the amount (weight) of the waste material being processed.

As the wet particles near the discharge end of the conveyor 34, the hepa-filter 40 removes and destroys any chemical fumes, airborne dust particles, odors, and bacteria.

The particles then drop into the second modified grinding/grating machine 43 which rotates at a substantially higher speed than the first machine (28) and further grinds, grates, and macerates the particles, reducing them to into particles of from ⅛" to ½" in size. In the second modified grinding/grating machine 43, the blade knives not only further reduce the size of the particles of waste material, but also force hot air from the heated grating plate through the particles to dry the particles. Drying is further facilitated by the vacuum or negative pressure in the grinding/grating machine 43 produced by the hepa-filter 40. The hepa-filter 40 also effectively captures and destroys chemical fumes, airborne dust particles, odors, and bacteria which may be present during and after the second grinding and grating operation. The resulting product is a dry, fluffy, confetti-like material and is unrecognizable as to the source.

The dry confetti-like material drops into the horizontal screw conveyor 45 which feeds it into the vertical screw conveyor 47. The vertical screw conveyor 47 swirls the dried confetti-like material in a spiral as it is transported vertically upward.

The dried confetti-like material enters the elongate tubular discharge screw conveyor 50 and is discharged through the discharge outlet 54 into the receptacle, such as a dumpster, compactor, or dump truck. It can then be safely transported to a landfill along with general waste from the health care facility.

Tests have shown that the present process using a sodium hypochlorite (NaOCl) disinfectant solution adjusted to a pH of about 4.0 to about 6.0 and final concentration of 2,500 ppm hypochlorous acid will produce at least a 4 $Log_{10}$ reduction or 99.99%, and in most cases, a 6 $Log_{10}$ reduction or 99.9999% reduction in the numbers of active microorganisms. The present system can also process from 1,500 to 3,000 pounds of waste per hour.

While this invention has been described fully and completely with special emphasis upon a preferred embodiment, it should be understood that within the scope of the appended claims the invention may be practiced otherwise than as specifically described herein.

We claim:

1. A method for processing and chemically disinfecting infectious waste material comprising the steps of:

transporting a wheeled enclosure containing lift and dumping means, a hopper, grinding and grating means, immersion vat means, conveyor means, suction and filter means, a source of power, a source of chemical disinfectant, and a source of fresh water, to a location where infectious waste material is stored;

placing said infectious waste material into a cart, placing said cart on said lift and dumping means, and dumping said infectious waste material into said hopper;

feeding said infectious waste material from said hopper to a first grinding and grating means and grinding and grating it into waste particles of a first size range;

immersing said waste particles in a chemical disinfectant contained in said immersion vat means;

after immersion, conveying said waste particles in a first enclosed screw conveyor from said vat means into a second high speed grinding and grating means rotating at a substantially higher speed than the rotation speed of said first grinding and grating means;

further grinding, grating, macerating, and drying said waste particles in said second high speed grinding and grating means to reduce said waste particles into a dry confetti-like material which is unrecognizable as to the source;

conveying said dry confetti-like material in a second enclosed screw conveyor system from said second high speed grinding and grating means to the exterior of said wheeled enclosure;

subjecting said first enclosed screw conveyor, said second grinding and grating means, and said second enclosed screw conveyor system to negative air pressure as said particles are being conveyed, ground, grated, macerated, and dried, and venting the air through a filter to remove chemical fumes, airborne dust particles, odors, and bacteria therefrom; and discharging said dry confetti-like material from said enclosed screw conveyor system into a receptacle.

2. The method according to claim 1 including the steps of spraying said previously immersed waste particles with at least one application of said chemical disinfectant as they are being conveyed in said first enclosed conveyor and further mixing said waste particles and said chemical disinfectant together as they are conveyed therein.

3. The method according to claim 1 wherein said step of immersing said waste particles in a chemical disinfectant comprises immersing said waste particles in a liquid solution of sodium hypochlorite (NaOCl) containing an effective concentration of hypochlorous acid (HOCl) sufficient to produce at least a 4 $Log_{10}$ reduction in the numbers of active microorganisms present in said waste particles.

4. The method according to claim 1 wherein said step of immersing said waste particles in a chemical disinfectant comprises immersing said waste particles in a liquid solution of sodium hypochlorite (NaOCl) adjusted to a pH in the range of about 4.0 to about 6.0 to produce a final concentration of 2,500 ppm hypochlorous acid (HOCl) which serves as the microbiocidal component of said disinfectant solution.

5. The method according to claim 1 wherein said step of grinding and grating said infectious waste material in said first grinding and grating means includes passing said infectious waste material through a set of rotating blades engaged with an apertured grate to grind, grate, and reduce said infectious waste material into said particles of a first size range.

6. The method according to claim 1 wherein said step of further grinding, grating, macerating, and drying said waste particles in said second high speed grinding and grating means includes passing said waste material through a set of rotating blades engaged with an apertured grate to grind, grate, macerate, and reduce said waste material into confetti-like particles which are unrecognizable as to the source.

7. The method according to claim 6 wherein said step of further grinding, grating, macerating, and drying said waste particles in said second high speed grinding and grating means includes drying said waste particles as they pass through said apertured grate by the heat produced by the friction of said rotating blades engaged with said apertured grate and the rotational speed of said blades.

* * * * *